US012806338B2

(12) United States Patent
Hopkins et al.

(10) Patent No.: US 12,806,338 B2
(45) Date of Patent: *Nov. 24, 2026

(54) VOLUME-BASED FLOW RATE COMPENSATION TECHNIQUE FOR INFUSION THERAPY

(71) Applicants: BAXTER INTERNATIONAL INC., Deerfield, IL (US); BAXTER HEALTHCARE SA, Glattpark (CH)

(72) Inventors: Patrick Michael Hopkins, Milwaukee, WI (US); Harry John Weber, Cary, IL (US); Haonan Sun, Milwaukee, WI (US)

(73) Assignees: BAXTER INTERNATIONAL INC., Deerfield, IL (US); BAXTER HEALTHCARE S.A., Glattpark (CH)

(*) Notice: Subject to any disclaimer, the term of this patent is extended or adjusted under 35 U.S.C. 154(b) by 323 days.

This patent is subject to a terminal disclaimer.

(21) Appl. No.: 18/435,095

(22) Filed: Feb. 7, 2024

(65) Prior Publication Data

US 2024/0173474 A1 May 30, 2024

Related U.S. Application Data

(63) Continuation of application No. 17/398,141, filed on Aug. 10, 2021, which is a continuation of application (Continued)

(51) Int. Cl.

*A61M 5/168* (2006.01)
*A61M 5/142* (2006.01)
*A61M 5/172* (2006.01)

(52) U.S. Cl.

CPC .... *A61M 5/16813* (2013.01); *A61M 5/14228* (2013.01); *A61M 5/14232* (2013.01);

(Continued)

(58) Field of Classification Search

CPC ...... A61M 2205/3379; A61M 5/14228; A61M 5/14232; A61M 5/16813; A61M 5/16877; A61M 5/16886

See application file for complete search history.

(56) References Cited

U.S. PATENT DOCUMENTS 4,137,011 A 1/1979 Rock
4,137,913 A 2/1979 Georgi (Continued)

FOREIGN PATENT DOCUMENTS

JP S59507663 A 4/1984
JP H03107930 A 5/1991

(Continued)

*Primary Examiner* — William R Carpenter

(74) *Attorney, Agent, or Firm* — Greer, Burns & Crain, Ltd

(57) ABSTRACT

An infusion pump for pumping fluid through an administrative set at a desired flow rate over a specified duration, and includes a pumping mechanism for releasably receiving and for exerting a pulsing force on the administrative set, thus pressurizing a portion of the set for creating a flow of fluid from a set outlet. A controller is connected to and is configured for operating the pumping mechanism, the controller determines a pulse frequency based on a volume of fluid infused over a portion of the specified duration and the desired flow rate, outputs a control signal to the pumping mechanism for operating the pumping mechanism based on the determined pulse frequency, determines a first pulse frequency based on the desired flow rate; and adjusts the first pulse frequency based on the volume of fluid infused to provide a second pulse frequency being different from the first pulse frequency.

15 Claims, 6 Drawing Sheets

Related U.S. Application Data

No. 15/892,207, filed on Feb. 8, 2018, now Pat. No. 11,116,895.

(60) Provisional application No. 62/457,648, filed on Feb. 10, 2017.

(52) U.S. Cl.
CPC .... *A61M 5/16831* (2013.01); *A61M 5/16877* (2013.01); *A61M 5/16886* (2013.01); *A61M 5/172* (2013.01); *A61M 2005/14208* (2013.01); *A61M 2205/3379* (2013.01); *A61M 2205/50* (2013.01); *A61M 2205/52* (2013.01); *A61M 2205/702* (2013.01)

(56) References Cited

U.S. PATENT DOCUMENTS

| | | | | |
|---|---|---|---|---|
| 4,291,692 | A | 9/1981 | Bowman et al. | |
| 4,534,756 | A | 8/1985 | Nelson | |
| 4,557,726 | A | 12/1985 | Reinicke | |
| 4,670,007 | A * | 6/1987 | Wheeldon | A61M 5/172 128/DIG. 13 |
| 4,832,689 | A | 5/1989 | Mauerer et al. | |
| 5,018,945 | A | 5/1991 | D'Silva | |
| 5,205,819 | A | 4/1993 | Ross et al. | |
| 5,399,166 | A | 3/1995 | Laing | |
| 6,489,896 | B1 | 12/2002 | Platt et al. | |
| 6,942,636 | B2 | 9/2005 | Holst et al. | |
| 6,966,895 | B2 | 11/2005 | Tribe | |
| 8,147,448 | B2 | 4/2012 | Sundar et al. | |
| 8,672,876 | B2 | 3/2014 | Jacobson et al. | |
| 8,911,403 | B2 | 12/2014 | Flachbart et al. | |
| 9,056,166 | B2 | 6/2015 | Zhu | |
| 10,865,786 | B2 | 12/2020 | Hungerford et al. | |
| 2005/0085760 | A1 | 4/2005 | Ware et al. | |
| 2006/0173412 | A1 | 8/2006 | Susi | |
| 2007/0077152 | A1 | 4/2007 | Knauper et al. | |
| 2009/0124963 | A1 * | 5/2009 | Hogard | A61M 1/15632 604/30 |
| 2011/0318198 | A1 * | 12/2011 | Johnson | F04B 49/065 417/300 |
| 2013/0177455 | A1 | 7/2013 | Kamen et al. | |
| 2017/0252512 | A1 | 9/2017 | Zhu | |

FOREIGN PATENT DOCUMENTS

| | | | |
|---|---|---|---|
| JP | H03184559 | A | 8/1991 |
| JP | 2011-177411 | A | 9/2011 |
| JP | 2015505258 | A | 2/2015 |
| JP | 2016503714 | A | 2/2016 |
| WO | 98/31935 | A1 | 7/1998 |
| WO | 02/070047 | A1 | 9/2002 |
| WO | 2013/096909 | A2 | 6/2013 |
| WO | 2014/100658 | A1 | 6/2014 |

* cited by examiner

VOLUME-BASED FLOW RATE COMPENSATION TECHNIQUE FOR INFUSION THERAPY

RELATED APPLICATION

This application is a continuation of U.S. patent application Ser. No. 17/398,141, filed on Aug. 10, 2021, which is a continuation of U.S. patent application Ser. No. 15/892,207 filed on Feb. 8, 2018, now U.S. Pat. No. 11,116,895, which in turns claims 35 U.S.C. § 119 Priority from U.S. Provisional Ser. No. 62/457,648 filed Feb. 10, 2017, all of which are incorporated by reference herein.

BACKGROUND

The present invention relates to systems used for medication delivery, and more particularly to a system designed for more accurately delivering medication through infusion therapy over a long duration.

Various medications may be provided to a patient via infusion therapy, which is conventionally practiced with an infusion pump such as a peristaltic pump. Peristaltic pumps typically operate by directly manipulating an administration set through which the medication is delivered. As is well known in the art, a main component of an infusion set is a length of plastic tubing, with fittings for connection to supplies of medication, saline solution or the like. The fittings are configured for receiving medication through gravity flow, or by injection, such as using a syringe. Over time, manipulation of the tubing causes a physical degradation of the administration set in the area manipulated by the infusion pump. That is, prolonged physical manipulation of the administration set by the peristaltic pump causes a reduction in springback or flexibility of the administration set tube, thereby reducing the fluid volume in each pumping cycle. Additionally, guidelines issued by the Centers for Disease Control suggest that an infusion pump should use the same administration set for no more than one week. Accordingly, infusion pump manufacturers provide pumps capable of accurately delivering the infusion fluid over a long duration (for example 72-96 hours). However, as discussed above, fatigue of the administration set results in significant error over time, since less fluid is actually pumped than would be predicted given the pump performance characteristics and the use of fresh tubing.

One solution to this decreased accuracy is to change administration sets more frequently. These frequent administration set changes, however, increase hospital costs by both increasing both physical resources consumed (i.e., more administration sets are used for each patient) and time required for patient care (i.e., a caregiver is required to spend more time with each patient due to more frequent administration set changes).

In the infusion therapy market, it is preferred to use administration sets made of hydrocarbon-based plastics, like PVC. One advantage is cost. PVC sets are simple and cheap to manufacture as they are generally extruded as a continuous piece of tubing. The continuous nature of the PVC set has the added benefit of providing a continuous sterile barrier throughout the set. An additional advantage of PVC sets is that they can be used interchangeably in pump-based therapies and in manual/gravity applications.

An alternative to PVC sets is sets made of polymer-based materials, such as silicone. These sets use a dedicated silicone pumping segment which is connected to non-pumping segments via joints. The silicone segment provides relatively consistent and accurate performance over the course of an infusion, compared to PVC tubing. However, the silicone segment and the connecting joints require more parts and assembly time, thereby increasing the cost of the set. Additionally, the extra joints increase the risk of fluid leaks and pose sterility concerns, compared to PVC-based sets. The silicone based sets are more difficult and expensive to use for a manual/gravity therapy.

Large Volume Parenteral (LVP) infusion pumps using sets made of materials like PVC display favorable accuracy for short term infusions. However, as described above, over long-duration infusions, the tubing loses resiliency, leading to under-infusion and flow rate accuracy drift. In each pumping cycle, there are two primary phases: the delivery phase and the fill phase. In the delivery phase, an active force is applied to the tubing by the pump mechanism to compress the tubing and move fluid downstream. During the fill phase, the pumping mechanism releases the tubing, allowing it to fill again. However, this process passively depends on the resiliency of the tubing to spring back to its full inner diameter and re-fill for the next cycle.

After repeated pumping cycles, the tubing undergoes permanent material property changes, which decrease its resiliency and in effect, the fill volume of each cycle. With the tubing unable to fill to its full volume, the maximum amount the pump can deliver each cycle is correspondingly limited, leading to under infusion and accuracy drift. This behavior is a function of the amount of pump cycles applied to the set.

The above performance degradation causes clinicians to either shift the location of the tube set in the pump channel to a "fresh section" during a therapy, potentially leading to an interruption in therapy; or to change sets more frequently, potentially causing interruption in therapy and/or increased risk of infection. The practice of moving the set after a short amount of time is currently recommended in pump operator manuals.

Although the problem of tubing degradation over time is well known in the industry, there have been a variety of approaches to find a medically effective and cost-efficient solution. Some infusion pump manufacturers have opted to improve accuracy by developing administration sets with a dedicated silicone pump segment. Silicone retains its resiliency and therefore maintains fill volume over many pump cycles. But while silicone tubing has improved accuracy over long durations, this strategy presents several significant drawbacks.

Sets with dedicated pumping and non-pumping segments have multiple junctions to join the segments together, thereby increasing manufacturing costs due to the added parts and assembly time/labor. While PVC sets are traditionally composed of a single, continuous piece of tubing, providing a sterile barrier through the length of the set, this option of using connecting joints in sets with dedicated pump segments increases the risk of fluid leaks and pose sterility concerns. Another drawback of silicone tubing sets is that in the manufacturing operation, potentially harmful curing agents are often used which could potentially leach into the fluid path of the tubing. Further, silicone is porous and can permit air ingress, posing a sterility concern.

Manufacturers have also addressed the problem of administration set tubing fatigue by modifying the pumping mechanism to actively move the tubing back into the filling position. One manufacturer has employed a shuttle mechanism which actively moves the tubing back into the filling position instead of passively relying on tubing resiliency. However, this modification added design and manufacturing complexity, cost, and weight to the pump. The added motion also requires more energy from the pump, which in turn diminishes the battery life of the device.

Still another approach to the tubing degradation problem involves software compensation, where a flow rate compensation algorithm was developed which accounted for Temperature, Back Pressure, and Flow Rate, as seen in the equation below.

$$PE=569P^2-4630P-129PT+2.3PF+15T^3-1283T^2+37510T+1TF-33F-363912$$

Where:

PE=Predictive Error;

P=Back Pressure;

T=Temperature; and

F=Flow Rate

While the exact value of the coefficients and power of the exponents in the above algorithm are unique to a particular infusion pump, only three factors were deemed to have significant impact on flow rate accuracy to warrant compensation: Temperature, Back Pressure, and Flow Rate. As evidenced by the magnitude of the coefficients and power of the exponents, the above algorithm deemed Temperature as having the most impact on flow rate accuracy, followed by Back Pressure and to an even lesser degree, Flow Rate having less impact on the accuracy. No other factors were compensated for.

Accordingly, there is a need for a simpler, more universal approach to the problem of infusion administrative tubing set degradation that is applicable to a wider range of infusion pumps.

SUMMARY

The above-listed need is met or exceeded by the present volume-based flow rate compensation for infusion therapy. The present invention is provided in the form of an improved infusion pump featuring a controller that is provided with improved operational software designed to adjust the infusion pump pulse frequency based on the volume infused through the administrative set. It has been found that by monitoring the volume of fluid infused, applying a Tubing Degradation Function that correlates historical tubing performance with volume infused, and adjusting the pulse frequency accordingly, the percent error of actual volume infused compared to pump target volume is relatively low compared to the conventional infusion pump systems described above. The technique applied by the present infusion pump is contrasted with conventional systems, where pulse frequency is adjusted based on correlating percent error as a function of time or flow rate.

An important feature of the present infusion pump and the benefit of the present volume-based flow rate accuracy compensation technique is that there is no cost once the software is developed and implemented. The cost of the pump will not increase since there are no parts added, hardware changed, or changes to manufacturing or service processes. Once the software is developed and implemented, there is no additional cost or investment required. There is also potential to apply this technique to a wide variety of infusion pumps.

The present infusion pump enables clinicians to use administration sets with materials like PVC for longer periods of time, thereby offering a huge cost and sales advantage over competitors with more expensive sets. Coupled with this is that there is no increase in the cost of the pump. Clinicians will no longer have to move the set after a short amount of time, reducing physical time and operational cost for the hospital or clinic. Also, adjusting flow rate as a function of volume provides a simple, generalized means of improving flow rate accuracy that is applicable irrespective of the programmed flow rate. Further, infusion pumps already have the capability of tracking volume infused, enabling simple implementation of the proposed technique.

More specifically, an infusion pump is provided that is configured for pumping fluid through a tubular administrative set at a desired flow rate over a specified duration, and includes a pumping mechanism constructed and arranged for releasably receiving the tubular administrative set and for exerting a pulsing force on the tubular administrative set, thus pressurizing a portion of the tubular administrative set for creating a flow of fluid from an outlet of the tubular administrative set. A controller is connected to the pumping mechanism and is configured for operating the pumping mechanism, the controller is configured to determine a pulse frequency based on a volume of fluid infused over a portion of the specified duration and the desired flow rate, output a control signal to the pumping mechanism for operating the pumping mechanism based on the determined pulse frequency, determining a first pulse frequency based on the desired flow rate; and adjusting the first pulse frequency based on the volume of fluid infused to provide a second pulse frequency, the second pulse frequency being different from the first pulse frequency.

In another embodiment, a method is provided for controlling a pumping mechanism of an infusion pump including a tubular administrative set and a pumping mechanism, the pumping mechanism being constructed and arranged for releasably receiving the tubular administrative set and for exerting a pulsing force on the tubular administrative set for creating a flow of fluid from an outlet of the tubular administrative set, the method controlling the pumping mechanism to pump fluid through the tubular administrative set at a desired flow rate over a specified duration. The method includes determining a pulse frequency based on a volume of fluid infused over a portion of the specified duration and the desired flow rate, outputting a control signal to the pumping mechanism for operating the pumping mechanism based on the determined pulse frequency, determining a first pulse frequency based on the desired flow rate, and adjusting the first pulse frequency based on the volume of fluid infused to provide a second pulse frequency, the second pulse frequency being different from the first pulse frequency.

In still another embodiment, an apparatus is provided, including computer-executable instructions stored on a non-transitory medium, wherein the instructions, when executed by a processor, cause the processor to: determine a volume of fluid infused from an outlet of a tubular administrative set of an infusion pump over a period of time, determine a pulse frequency based on the determined volume of fluid infused over the period of time and a desired flow rate of fluid infused from the outlet of the tubular administrative set; and outputting a control signal to a pumping mechanism for operating the pumping mechanism based on the determined pulse frequency, wherein the pumping mechanism is constructed and arranged for releasably receiving the tubular administrative set and for exerting a pulsing force on the tubular administrative set for creating a flow of fluid from the outlet of the tubular administrative set.

In yet a further embodiment, an infusion pump configured for pumping fluid through a tubular administrative set at a desired flow rate over a specified duration is provided. The infusion pump includes a pumping mechanism constructed and arranged for releasably receiving the tubular administrative set and for exerting a pulsing force on the tubular administrative set, thus pressurizing a portion of the tubular administrative set for creating a flow of fluid from an outlet of the tubular administrative set. The infusion pump also includes a controller connected to said pumping mechanism and configured for operating said pumping mechanism. The controller is configured to: determine a first pulse frequency to obtain a target fluid volume of fluid infused over a portion of the specified duration and the desired flow rate; output a control signal to said pumping mechanism for operating said pumping mechanism at said first pulse frequency; and adjust the first pulse frequency to a second pulse frequency, said second pulse frequency being different from said first pulse frequency. Adjusting the first pulse frequency includes adjusting the first pulse frequency at predetermined volume points based on a comparison of historical data of administrative set flow rate accuracy in terms of % error with an intended volume of fluid infused, such that said second pulse frequency compensates for the degradation of the material of the administrative set.

In a further embodiment, a method for controlling a pumping mechanism of an infusion pump including a tubular administrative set and a pumping mechanism is provided. The pumping mechanism is constructed and arranged for releasably receiving the tubular administrative set and for exerting a pulsing force on the tubular administrative set, thus pressurizing a portion of the tubular administrative set for creating a flow of fluid from an outlet of the tubular administrative set. The method controls the pumping mechanism to pump fluid through the tubular administrative set at a desired flow rate over a specified duration. A controller is connected to said pumping mechanism and configured for operating said pumping mechanism. The method includes using the controller to: determine a first pulse frequency to obtain a target fluid volume of fluid infused over a portion of the specified duration and the desired flow rate; output a control signal to said pumping mechanism for operating said pumping mechanism at said first pulse frequency; and adjust the first pulse frequency to a second pulse frequency, said second pulse frequency being different from said first pulse frequency. Adjusting the first pulse frequency includes adjusting the first pulse frequency at predetermined volume points based on a comparison of historical data of administrative set flow rate accuracy in terms of % error with an intended volume of fluid infused, such that said second pulse frequency compensates for the degradation of the material of the administrative set.

DETAILED DESCRIPTION

Figure 1:
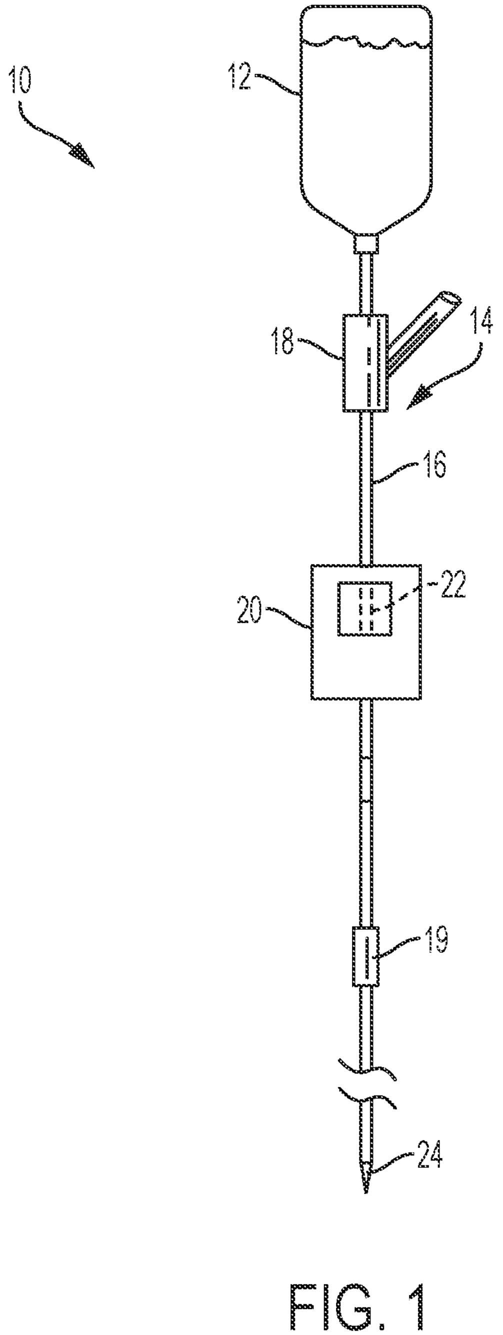
FIG. 1 is a front elevation of the present infusion pump connected to an administrative tubing set.
Figure 2:
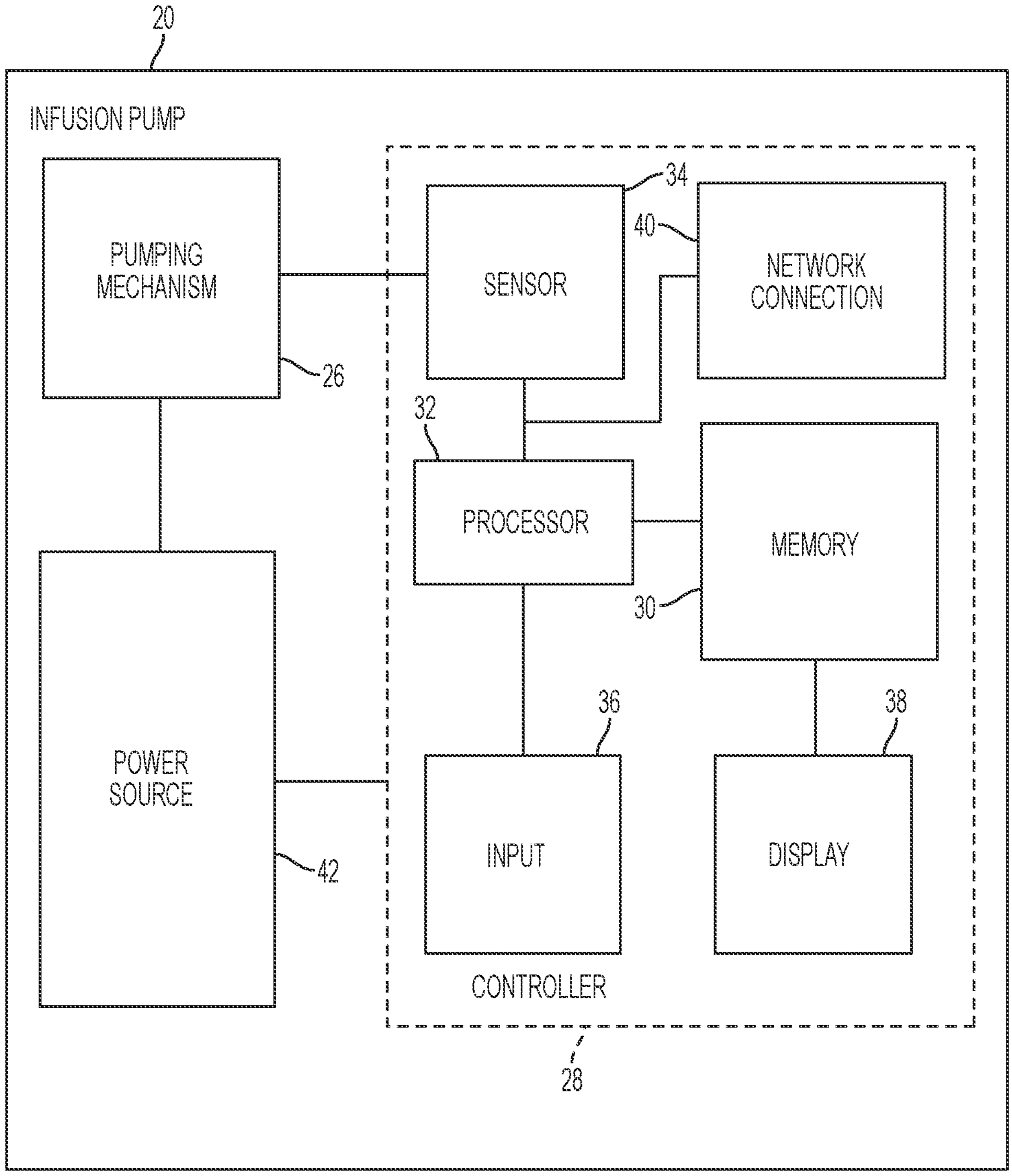
FIG. 2 is a schematic diagram of the present infusion pump.

Referring now to FIGS. 1 and 2, an infusion pump fluid transfer system is generally designated 10. The infusion system 10 is designed for use in dispensing medication, stored in a medication container 12, typically a bag, bottle, syringe, or other standard container used to contain liquid medications. There is no particular restriction regarding what containers 12 may be used. As is known in the art, the medication container 12 is connected to an administration set or tubing set 14, including a length of flexible plastic tubing 16 and at least one optional luer fitting 18 through which a medical practitioner inserts supplemental fluids, such as complementary medications and the like prior to administration to the patient. As is known in the art, the administration set 14 is optionally provided with other fittings and connections, including but not limited to line clamps 19.

An infusion pump 20 has a chamber 22 for receiving a portion of the tubing 16 and exposing the portion to a periodic pulsing or pressing force designed to force a discrete volume of the liquid through the tubing. Ultimately the tubing 16 is connected to an administration set outlet, also referred to as a catheter 24 for connection to a patient. The catheter 24 is contemplated as being any standard equipment for use with a patient. For example, catheters 24 include a temporary catheter inserted into a peripheral vein, a peripherally inserted central catheter, a central venous catheter, or other catheter known to those in the art.

As shown in FIG. 2, the infusion pump 20 is any known pump used to administer fluid intravenously. The pump 20 is used to help regulate fluid flow through the system 10, and may be used to vary an infusion rate based on, for example time and/or patient demand. The pump 20 may include one or more "channels," with each channel used to regulate fluid flow from a distinct medication container through a distinct tubing set.

Referring now to FIG. 2, the infusion pump 20, such as a linear peristaltic infusion pump or the like well-known in the art, is shown schematically. The infusion pump 20 includes at least a pumping mechanism 26 configured for generating periodic pulses which compress the portion of tubing 16 located in the chamber 22. Signals for controlling the pumping mechanism 26 are generated by a controller 28, such as a computerized device having at least a memory 30, a processor 32, one or more sensors 34, an input device 36, a display 38, and preferably a network or other communication interface 40. A power source 42 is preferably also incorporated into the infusion pump 20.

The pumping mechanism 26 may be any pump mechanism useful to facilitate fluid flow in a large-volume infusion pump. As a non-limiting example, a linear peristaltic pump is considered suitable. Other non-limiting examples include multi-finger peristaltic pumping mechanisms; single finger peristaltic pumping mechanisms and rotary pumps that act along a tube length to propel fluid through a tube. The controller 28 is preferably incorporated into the infusion pump 20, and is used to control the pumping mechanism 26. More specifically, the controller 28 is connected to the pumping mechanism 26 and is configured for determining a pulse frequency exerted on the tubing set 14.

It is preferable that the memory 30 is a non-transitory computer-readable recording medium, such as a read only memory (ROM), random access memory (RAM), hard disk, non-volatile flash memory or other electronically erasable programmable read-only memories (EEPROMs), or optical or magneto-optical memory storage media. Preferably, the memory 30 stores at least instructions which, when executed, facilitate control of the pumping mechanism 26. The processor 32 is preferably a microprocessor or other central processing unit capable of executing the instructions stored in the memory 30.

The controller 28 also includes the one or more sensors 34 used to monitor at least one characteristic value relating to a status of the infusion pump 20. Non-limiting examples of this characteristic value include an amount of time that has elapsed during the infusion process, and the intended volume of liquid dispensed through the administration set 14 loaded in the infusion pump 20. Those of skill in the art will recognize that other characteristic values may be monitored without departing from the scope of this invention. Because each of the sensors 34 monitors a characteristic value related to the pumping process of the infusion pump, the sensors are operably connected to the pumping mechanism 26.

A keypad or similar device that accepts data input by a user serves as the input device 36. The display 38 is preferably a liquid crystal display, cathode ray tube, plasma display, or other device capable of outputting data from the memory and processor in a way that is easily discernible by a user. Alternatively, the input device 36 and the display 38 may be incorporated into a single input/output device such as a touch screen display. The input device 36 and/or the display 38 are optionally integral with the infusion pump 20, or may be separate from, but connected to the infusion pump, provided that the input device and/or the display are configured for bi-directional communication with the infusion pump.

The network communication interface 40 allows the infusion pump 20 to connect to a local area network (LAN), wide area network (WAN), and/or the Internet. The network connection may be a wired connection using, for example, the IEEE 802.3 standard, or a wireless connection using standards such as IEEE 802.11 a/b/g/n/ac, or any newly developed standards that supersede these. Additionally, the network connection 40 may connect to a cellular/mobile data network using a protocol such as LTE, WiMAX, UMTS, CDMA, HSPA, HSPA+, GPRS, and the like.

The power source 42 is any known power source sufficient to provide power to both the pumping mechanism 26 and the controller 28. As non-limiting examples, the power source 42 may include one or more of a battery, a fuel cell, and a connection to a power line.

In operation, the pump 20 is used to convey fluid from the upstream source container 12, through the tubing 16 of the administration set 14 in a downstream direction towards and into a patient through the catheter 24 or access site. Conventional peristaltic pumps rely on one or more fingers or occluders sequentially compressing a pumping portion of the flexible tube 16. With a primed tube (one already filled with fluid) the upstream occluder compresses the tube 16, followed in sequence by the next downstream occluder, until each of the occluders present has compressed the tube. As the occluders apply pressure to the tube 16, the portion of tube under compression is pinched closed (occluded), thus forcing the fluid to move downstream through the tube. When compression by all of the occluders is complete or nearly complete, the upstream occluder begins to re-open, or decompress, the tube 16. The opening of the occluders also occurs sequentially from the upstream direction towards the downstream direction. As the tube 16 decompresses or re-opens to its natural state after release of the occluder, fluid flows into the pumping section of the tube from the source container 12 under the force of gravity and ambient pressure. The extent to which the pumping section of the tube 16 re-opens depends upon the current elasticity of the pumping section of the tube. Therefore, the amount of fluid that flows into the pumping section as or after the occluders have opened is also dependent upon the elasticity of the pumping section of the tube 16.

However, over time, the mechanical manipulation of the flexible tube 16 by the occluders leads to a physical breakdown of the tube, whereby the flexible tube no longer fully re-opens to its original shape. The pump controller 28 is programmed to monitor the intended volume of liquid dispensed as a function of the tube diameter and the number of pulses or occlusions, also referred to as pulse frequency, in view of the performance of a new, fresh tube 16. Accordingly, as the tube 16 degrades through continued flexing, over time, the fluid volume moved through each cycle of the pump 20 is reduced, leading to an overall reduction in the infusion fluid provided to a patient. Moreover, traditional infusion pumps rely on an open-loop control to maintain a flow rate by maintaining pulse rate, and do not take this reduction in provided volume into account. Accordingly, pump accuracy degrades over time. It should be noted that in the above described sequence of compression by the occluders, at all times, at least one occluder remains compressed at any given time to prevent a free-flow condition as is known in the art. Also, the pumping may be accomplished with a single occluding member. This case would include that addition of an upstream valve located upstream of the occluding member and a downstream valve located downstream of the occluding member. Compression and release of the upstream valve, occluding member and downstream valve are sequenced as is known in the art to achieve the desired fluid movement.

After the administration set 14 is properly loaded into the infusion pump 20, the material used to form the administration set is specified. This may require a manual specification by the user, such as through an entry of the specific material (e.g., PVC plasticized with either DEHP or non-DEHP plasticizers, polyethylene, silicone etc.) and/or a model number corresponding to the loaded set using the input device. Alternatively, some embodiments may include, as in input device, a reader capable of reading a barcode, QR code, or other similar machine-readable code to input the model of the administration set. Still other embodiments of the infusion pump are suitable for use with only administration sets formed from a particular material, or with only a particular model of administration set. In this case, the material is specified automatically, or presumed, without requiring user interaction.

A main feature of the present infusion pump 20 is that the pump controller 28, not only determines the pulse frequency exerted on the tubing set 16 for obtaining a desired or target volume of dispensed liquid, but is also provided with an algorithm or mathematical function, referred to as a Tubing Degradation Function, and is constructed and arranged to adjust the pulse frequency according to the Tubing Degradation Function for obtaining a target fluid volume dispensed by the administrative set.

In operation, over the course of the infusion, the pump speed or pulse frequency is adjusted (i.e faster or slower) by a predetermined amount to compensate for diminished performance, degradation and material property change in the administration set. The predetermined amount is calculated based on historical data that correlates flow rate accuracy (%

Error) with volume infused, as opposed to correlating % Error as a function of time or flow rate, as has previously been done in other applications.

Data and Tests Conducted

Figure 3:
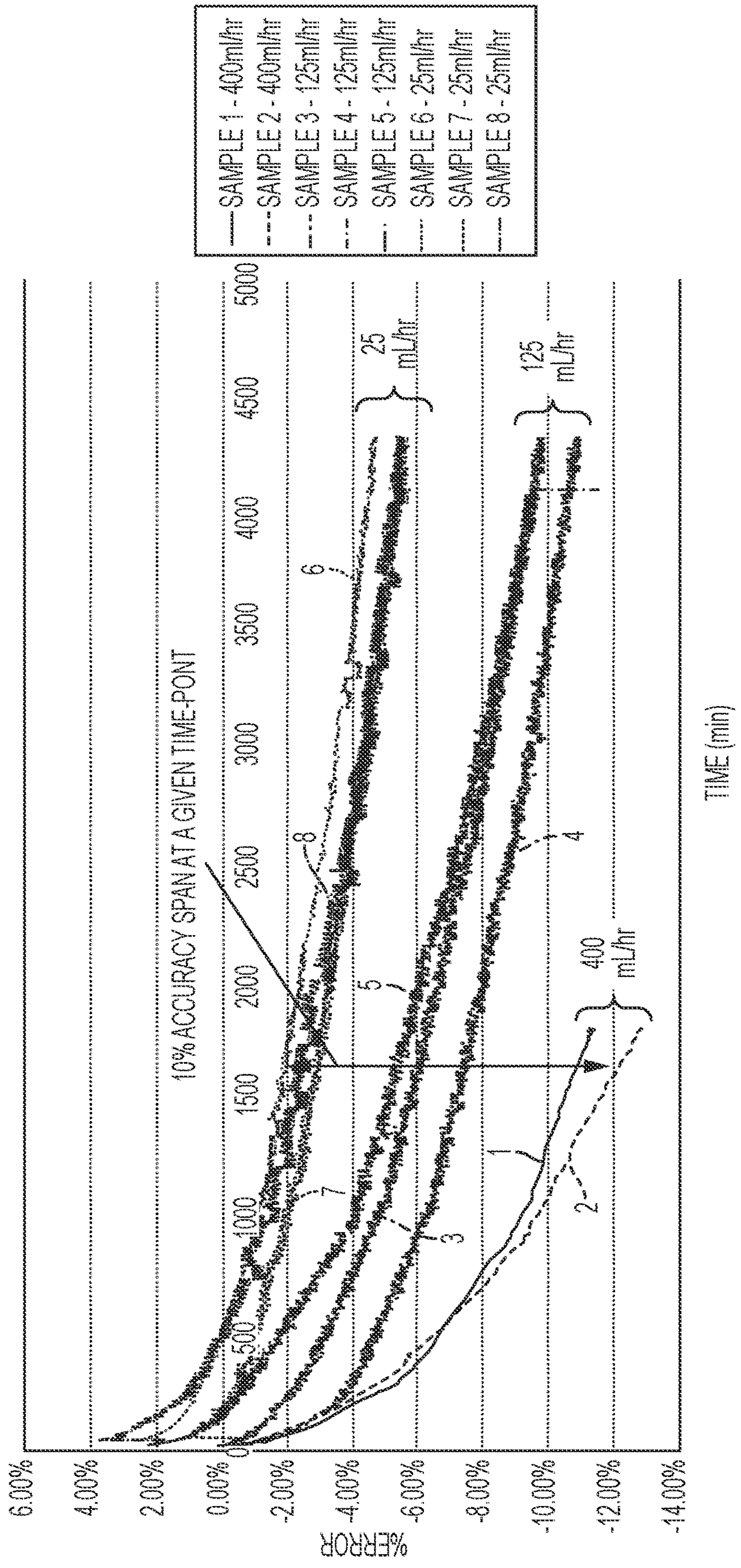
FIG. 3 is a graph of Performance Accuracy Percent Error vs. Infusion Time.
Figure 4:
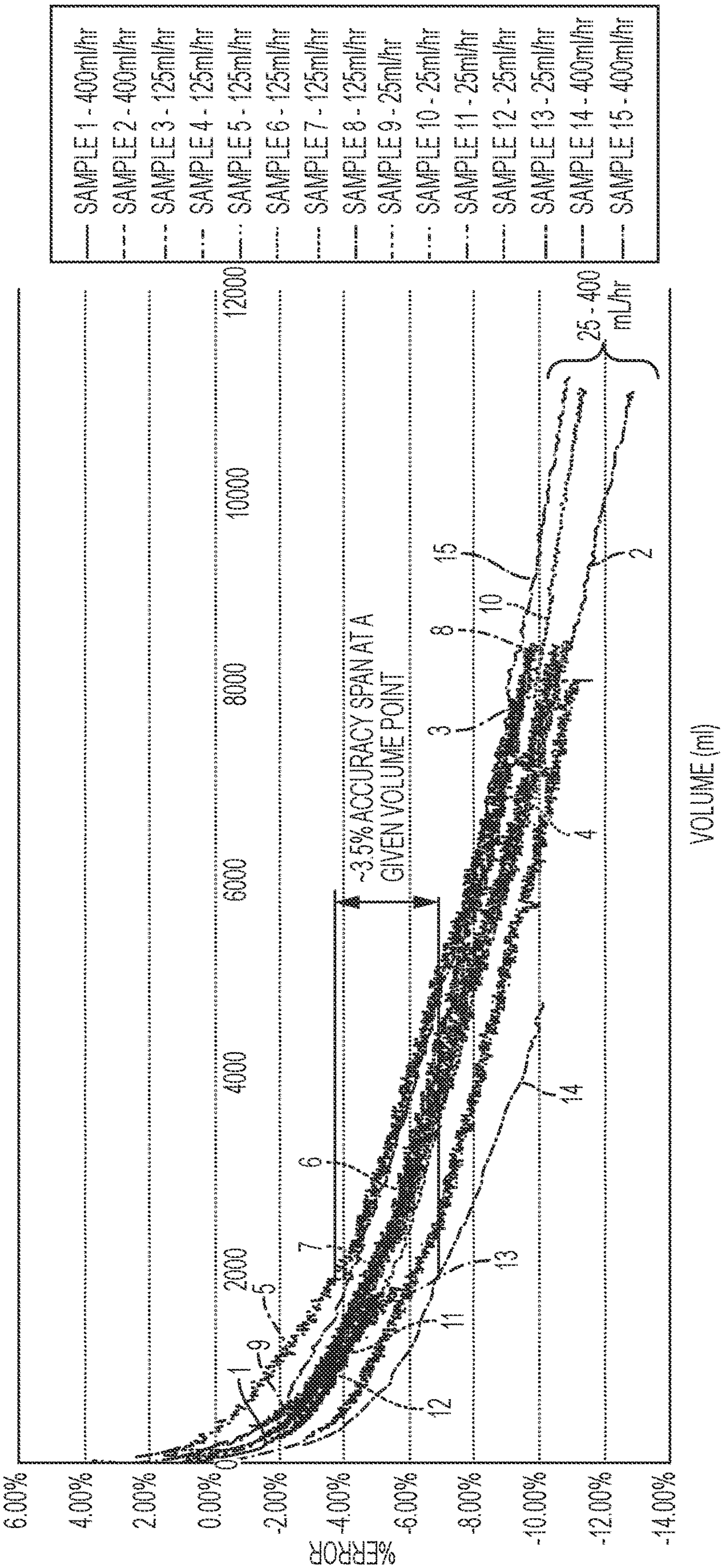
FIG. 4 is a graph of Performance Accuracy Percent Error vs. Infusion Volume.

Referring now to FIGS. 3 and 4, three different flow rates (25, 125, and 400 mL/hr) were tested using the same conditions (fluid infused, product code), manufacturing lot, environmental conditions, head height). Infusion duration differed for each test in order to test to the clinically appropriate limits of 72 hours or 12 L, whichever comes first. Flow rate data was gathered and flow rate accuracy was assessed using a 1 hour moving average at each time-point in order to capture the accuracy of each hour of infusion.

Data Analysis

As seen in FIG. 3, plotting flow rate accuracy (% Error) of the selected flow rates as a function of time yields a wide spread of the data and no reliable trend that could be used to adjust for changes in performance. At any given time point, the accuracy between flow rates could vary as much as 10%, rendering a time-based adjustment ineffective.

Referring now to FIG. 4, the present pump controller 28 is configured for compensating for administrative set tubing degradation by adjusting pulse frequency based on volume infused, as opposed to time-based adjustment. In FIG. 4, plots are depicted of the same accuracy data as FIG. 3, but instead of time as the x-axis, the data was plotted against volume infused. The results show highly consistent behavior correlating % Error to volume infused, irrespective of programmed flow rate. At any given volume point, the difference in accuracy between flow rates is at a maximum of around 3.5% (roughly 3 times more consistent than the time-based approach), allowing this technique to be applied generally across the anticipated infusion rates of the pump.

Using the trend depicted in FIG. 4, an algorithm can be developed to adjust the pump speed over the course of the infusion based on volume infused. The technique can be applied generally for a wide range of flow rates, as is evidenced by the consistency in the data which spans from 25-400 mL/hr. Additionally, the predominant input to the compensation algorithm is "volume infused", which infusion pumps currently track, enabling simple implementation.

It will be appreciated that the present system contemplates that there will be performance variations from tube-to-tube, so that no two samples of the same type of tubing set will perform identically. Similarly, individual infusion pumps of a particular manufacturer's model number will experience slight performance differences. Despite these differences, the present pump employing a volume-based control regimen has been found to achieve relatively consistent performance across a variety of flow rates, as opposed to a time-based control regimen. As seen in FIG. 4, there is a 3.5% span of accuracy at a particular preset volume, compared to the 10% span at a given time shown in FIG. 3.

As far as generating the Tubing Degradation Function, using empirical data, a correlation between flow rate accuracy and infused volume can be established. Then, a lookup table can be generated to store infusion volume (V1, V2, . . . Vn), the error value at that infusion volume, (E1, E2, . . . En) and the corresponding adjustment value for the predicted error (A1, A2, . . . An). Once the pump has infused a volume, Vn which corresponds to a known undesirable accuracy, En, the pump will then adjust the flow rate by the adjustment value, An, in order to maintain the flow rate accuracy within a desired range (Table 1). Accordingly, the adjustment value takes the form of the Tubing Degradation Function, which causes the pump to operate at an adjusted pulse frequency, distinct from the original frequency programmed into the pump. It will be appreciated that the adjusted pulse frequency is optionally periodically updated as the target volume is dispensed.

TABLE 1

| Volume Infused | Error Value | Adjustment Value |
|---|---|---|
| V1 | E1 | A1 |
| V2 | E2 | A2 |
| . . . | . . . | . . . |
| Vn | En | An |

Figure 5:
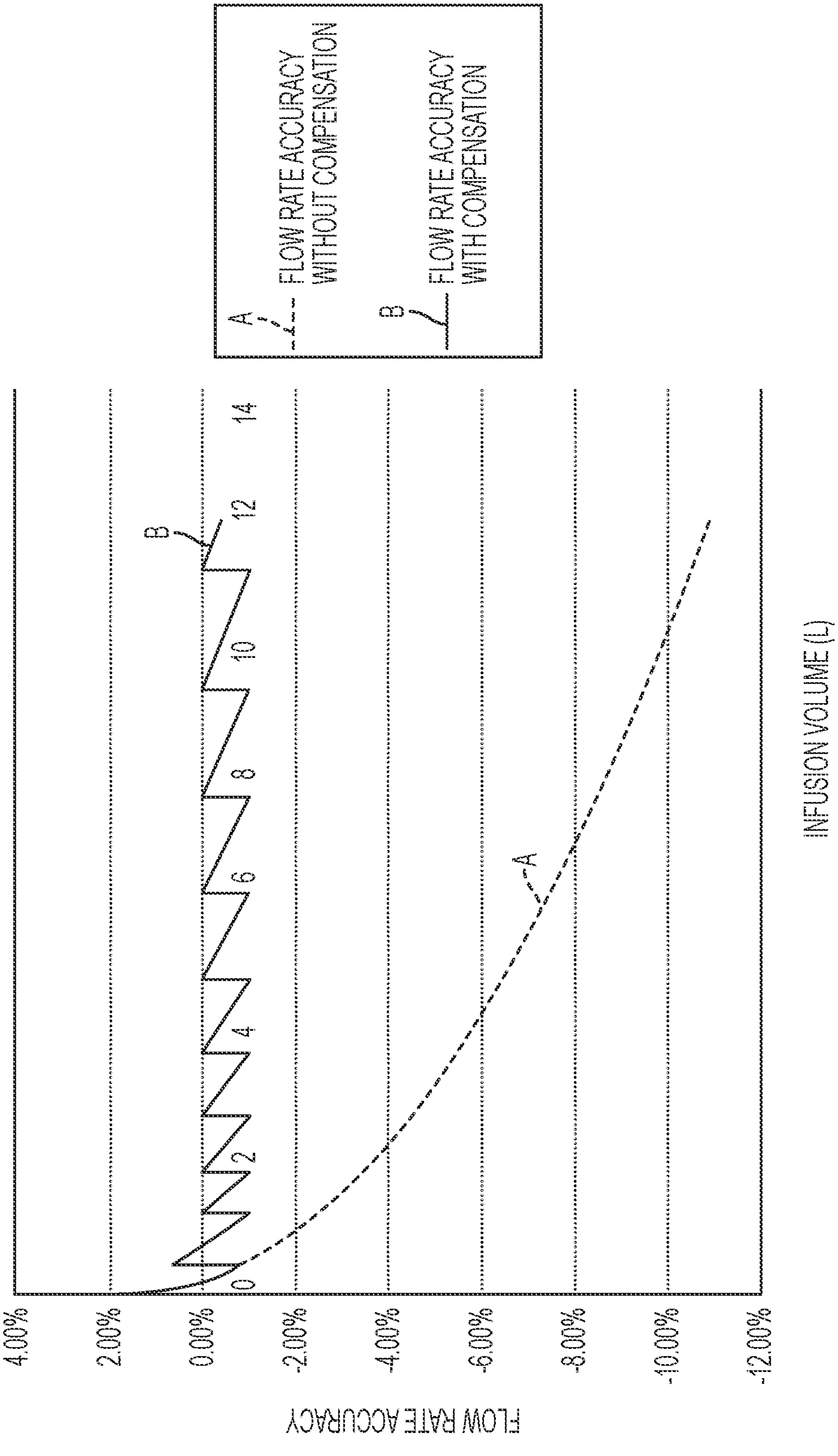
FIG. 5 is a graph of the data-generated curve used for providing an initial version of the Tubing Degradation Function.
Figure 6:
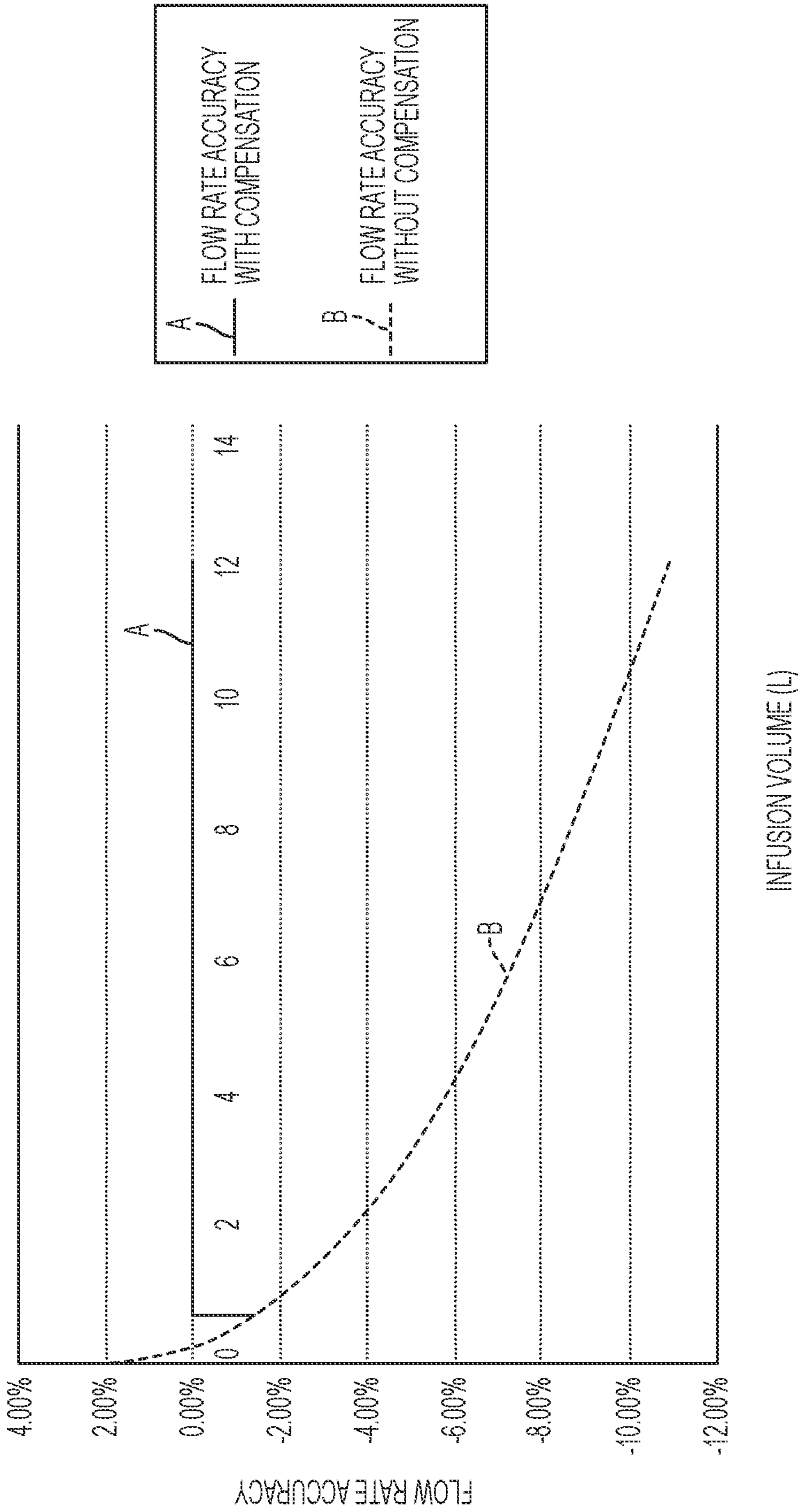
FIG. 6 is a graph of the basic curve of FIG. 5 which has been adjusted using empirical data and provides a more accurate format for conversion into the desired function for conversion into an algorithm suitable for use in the controller.

Referring now to FIGS. 5 and 6, as an alternative technique, using empirical data, a correlation between flow rate accuracy and infused volume can be established, as shown at FIG. 5. Then, at predetermined volume points over the course of the infusion, the pump rate will be adjusted by known amounts in order to maintain the flow rate accuracy within a desired range. As seen in FIG. 6, the data of FIG. 5 is subjected to fine adjustment by using empirical data, a correlation between flow rate accuracy and infused volume can be established, generating a compensation equation which becomes the Tubing Degradation Function. The pump, which already tracks infusion volume, will adjust the infusion rate in the form of changing the pulse frequency based on the Tubing Degradation Function at a pre-determined interval, providing continuous adjustment to compensate for flow rate error. Thus, the adjusted pulse frequency is contemplated as changing over the course of the infusion.

While a particular embodiment of the volume-based flow rate compensation for infusion therapy has been described herein, it will be appreciated by those skilled in the art that changes and modifications may be made thereto without departing from the invention in its broader aspects and as set forth in the following claims.

The invention claimed is:

1. An infusion pump configured for pumping fluid through a tubular administrative set at a desired flow rate over a specified duration, comprising:

a pumping mechanism releasably receiving the tubular administrative set and configured to exert a force on the tubular administrative set to create a flow of fluid from an outlet of the tubular administrative set; and a controller connected to said pumping mechanism and configured for operating said pumping mechanism;

said controller being configured to:

determine a first pulse frequency to obtain a target fluid volume of fluid infused over a portion of the specified duration and the desired flow rate;

determine a second pulse frequency based on the target fluid volume of fluid infused over a portion of the specified duration and the desired flow rate, said second pulse frequency being different from said first pulse frequency;

output a control signal to said pumping mechanism for operating said pumping mechanism at said first pulse frequency;

and output a second control signal to said pumping mechanism for operating said pumping mechanism at said second pulse frequency to compensate for a degradation of a material of the administrative set, wherein said second pulse frequency is determined by comparing historical data of administrative set flow rate accuracy in terms of % error with an intended volume of fluid infused.

2. The infusion pump of claim 1, wherein said controller is further configured to determine the intended volume of fluid infused over the portion of the specified duration based on a received input.

3. The infusion pump of claim 1, wherein said controller is further configured to:

store, in a memory as stored information, the intended volume of fluid infused, an error value at the intended volume of fluid infused, and an adjustment value for the error value; and, generate a lookup table from the stored information.

4. The infusion pump of claim 1, wherein said first pulse frequency is greater than said second pulse frequency.

5. The infusion pump of claim 1, wherein said first pulse frequency is less than said second pulse frequency.

6. The infusion pump of claim 1, further comprising:

a sensor connected to said pumping mechanism for sensing a volume of fluid infused from the tubular administrative set.

7. The infusion pump of claim 1, wherein said controller comprises:

a processor;

a memory connected to said processor; and non-transitory instructions stored in said memory and executable by said processor for causing said processor to:

determine said second pulse frequency; and output the second control signal to said pumping mechanism for operating said pumping mechanism at said second pulse frequency.

8. The infusion pump of claim 7, wherein said second pulse frequency is also based on a geometric attribute of a tube of the tubular administrative set.

9. The infusion pump of claim 1, wherein said second pulse frequency is based on, in part, a geometric attribute of a tube of the tubular administrative set.

10. The infusion pump of claim 1, wherein said second pulse frequency is determined by using a Tubing Degradation Function compiled based on a comparison of historical data of administrative set flow rate accuracy in terms of % error with volume of fluid infused compared with a target pump volume.

11. The infusion pump of claim 10, wherein said controller is further configured to receive an input from a sensor representing a volume of fluid infused from the tubular administrative set.

12. The infusion pump of claim 10, wherein said controller is further configured to receive an input as to the type of material used to form the administrative set.

13. An infusion pump configured for pumping fluid through a tubular administrative set at a desired flow rate over a specified duration, comprising:

a pumping mechanism releasably receiving the tubular administrative set and configured to exert a force on the tubular administrative set to create a flow of fluid from an outlet of the tubular administrative set; and a controller connected to said pumping mechanism and configured for operating said pumping mechanism;

said controller being configured to:

determine a first pulse frequency to obtain a target fluid volume of fluid infused over a portion of the specified duration and the desired flow rate;

determine a second pulse frequency based on the target fluid volume of fluid infused over a portion of the specified duration and the desired flow rate, said second pulse frequency being different from said first pulse frequency;

output a control signal to said pumping mechanism for operating said pumping mechanism at said first pulse frequency;

and output a second control signal to said pumping mechanism for operating said pumping mechanism at said second pulse frequency to compensate for a degradation of a material of the administrative set, wherein said second pulse frequency is determined by using a Tubing Degradation Function compiled based on a comparison of historical data of administrative set flow rate accuracy in terms of % error with volume of fluid infused compared with a target pump volume.

14. The infusion pump of claim 13, wherein said controller is further configured to receive an input from a sensor representing a volume of fluid infused from the tubular administrative set.

15. The infusion pump of claim 13, wherein said controller is further configured to receive an input as to the type of material used to form the administrative set.

* * * * *